United States Patent
Wulff et al.

(10) Patent No.: US 7,348,460 B2
(45) Date of Patent: *Mar. 25, 2008

(54) METHOD FOR PRODUCING ALKANOL ALKOXYLATES AT OPTIMAL REACTION TEMPERATURES

(75) Inventors: Christian Wulff, Mannheim (DE); Michael Stoesser, Neuhofen (DE); Georg Heinrich Grosch, Bad Duerkheim (DE); Kai-Uwe Baldenius, Ludwigshafen (DE); Edward Bohres, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/527,529

(22) PCT Filed: Apr. 25, 2003

(86) PCT No.: PCT/EP03/04331

§ 371 (c)(1),
(2), (4) Date: Mar. 11, 2005

(87) PCT Pub. No.: WO2004/033403

PCT Pub. Date: Apr. 22, 2004

(65) Prior Publication Data

US 2006/0052648 A1    Mar. 9, 2006

(30) Foreign Application Priority Data

Sep. 18, 2002  (DE) ................................ 102 43 362

(51) Int. Cl.
C07C 41/03 (2006.01)
C08F 4/02 (2006.01)

(52) U.S. Cl. ...................................................... 568/618
(58) Field of Classification Search ................. 568/618
See application file for complete search history.

(56) References Cited

U.S. PATENT DOCUMENTS

| 2,508,036 | A | 5/1950 | Kosmin |
| 6,429,342 | B1 * | 8/2002 | Clement et al. ............ 568/616 |
| 7,196,030 | B2 * | 3/2007 | Wulff et al. ................ 502/104 |
| 2006/0004232 | A1 * | 1/2006 | Wulff et al. ................ 568/679 |

FOREIGN PATENT DOCUMENTS

| DE | 102 18 752 | 11/2003 |
| DE | 102 18 753 | 11/2003 |
| DE | 102 18 754 | 11/2003 |
| EP | 0 775 716 | 5/1997 |
| EP | 0 862 977 | 9/1998 |
| EP | 0 892 002 | 1/1999 |
| WO | 94 11330 | 5/1994 |
| WO | 94/11331 | 5/1994 |
| WO | 00 74845 | 12/2000 |
| WO | 01/04183 | 1/2001 |

* cited by examiner

Primary Examiner—Rosalynd Keys
(74) Attorney, Agent, or Firm—Oblon, Spivak, McClelland, Maier & Neustadt, P.C.

(57) ABSTRACT

The present invention relates to a process for preparing at least one alkoxylate, which comprises bringing at least one alkylene oxide selected from the group consisting of ethylene oxide, propylene oxide, butylene oxide, pentylene oxide and decene oxide into contact with at least one starter compound in the presence of at least one double metal cyanide compound, with the reaction being carried out at a temperature of from 130° C. to 155° C., to the alkoxylates, in particular ethoxylates, themselves and to the use of such ethoxylates as emulsifier, foam regulator or as wetting agents for hard surfaces.

8 Claims, No Drawings

METHOD FOR PRODUCING ALKANOL ALKOXYLATES AT OPTIMAL REACTION TEMPERATURES

The present invention relates to a process for preparing at least one alkoxylate, which comprises bringing at least one alkylene oxide selected from the group consisting of ethylene oxide, propylene oxide, butylene oxide, pentylene oxide and decene oxide into contact with at least one starter compound in the presence of at least one double metal cyanide compound, with the reaction being carried out at a temperature of from 130° C. to 155° C., to the alkoxylates, in particular ethoxylates, themselves and to the use of such ethoxylates as emulsifier, foam regulator or as wetting agents for hard surfaces.

It is known from the literature that double metal cyanide compounds (DMC compounds) can be used as catalysts for the reaction of starter molecules having an active hydrogen and alkylene oxides, for example in a polymerization reaction. The ring-opening polymerization of alkylene oxides is described, for example, in EP-A 0 892 002, EP-A 0 862 977 and EP-A 0 775 716. DMC compounds display a high activity as catalyst in the polymerization of alkylene oxides.

Processes for the alkoxylation of aliphatic alcohols and the alkoxylates obtained are known in principle from the prior art. For example, WO 01/04183 describes a process for the ethoxylation of hydroxy-functional starter compounds which is carried out in the presence of a double metal cyanide compound as catalyst.

Alkoxylates of aliphatic alcohols are used widely as surfactants, emulsifiers or antifoams. The wetting and emulsifying properties depend strongly on the type of alcohol and the type and amount of the alkoxide adducts.

WO 94/11330 relates to alkoxylates of 2-propylheptanol and their use. The alkoxylates comprise 2-propylheptanol which has firstly been reacted with from 1 to 6 mol of propylene oxide and then with from 1 to 10 mol of ethylene oxide in the presence of alkali metal hydroxides as catalysts. According to the examples, a 2-propylheptanol which has been reacted firstly with 4 mol of propylene oxide and then with 6 mol of ethylene oxide is used. It is stated that the alkylene oxide adducts display an improved ratio of foam behavior to detergent action. It is also stated that the alkoxylates display good wetting behavior. They are used in detergent compositions for cleaning textile materials. WO 94/11331 relates to the use of such alkoxylates.

U.S. Pat. No. 2,508,036 likewise relates to the use of 2-n-propylheptanol ethoxylates comprising from 5 to 15 mol of ethylene oxide as wetting agents in aqueous solution. It is stated that the products can be used as surfactants in laundry detergents.

DE-A-102 18 754 and DE-A-102 18 753 relate to the use of $C_{10}$-alkanols alkoxylate mixtures, in particular alkanol ethoxylate mixtures, to such $C_{10}$-alkanol alkoxylate mixtures and to processes for preparing them. DE-A-102 18 752 likewise describes alkoxylate mixtures and laundry detergents in which these are present and also processes for preparing the alkoxylate mixtures and the use of the laundry detergent for washing or cleaning textiles.

Two difficulties in particular occur in the alkoxylation, in particular the ethoxylation, of starter compounds in the presence of double metal cyanide compounds. Firstly, the induction phase of the reaction is sometimes very long, which leads to a prolonging of the reaction times and to increased costs, and secondly the activity of the catalyst frequently decreases slowly during the reaction until the reaction rate is no longer satisfactory. The reaction therefore does not process to completion and the products obtained contain impurities, for example residues of the starter compound.

It was therefore an object of the present reaction to provide a process for the alkoxylation of starter compounds which has improved reaction rates, improved conversion, improved catalyst stability and a shortened induction time.

This object is achieved according to the invention by a process for preparing at least one alkoxylate, which comprises bringing at least one alkylene oxide selected from the group consisting of ethylene oxide, propylene oxide, butylene oxide, pentylene oxide and decene oxide into contact with at least one starter compound in the presence of at least one double metal cyanide compound of the general formula I:

$$M^1_a[M^2(CN)_b(A)_c]_d \cdot fM^1_gX_n \cdot h(H_2O) \cdot eL \cdot kP \qquad (I),$$

where $M^1$ is at least one metal ion selected from the group consisting of $Zn^{2+}$, $Fe^{2+}$, $Fe^{3+}$, $Co^{3+}$, $Ni^{2+}$, $Mn^{2+}$, $Co^{2+}$, $Sn^{2+}$, $Pb^{2+}$, $Mo^{4+}$, $Mo^{6+}$, $Al^{3+}$, $V^{4+}$, $V^{5+}$, $Sr^{2+}$, $W^{4+}$, $W^{6+}$, $Cr^{2+}$, $Cr^{3+}$, $Cd^{2+}$, $Hg^{2+}$, $Pd^{2+}$, $Pt^{2+}$, $V^{2+}$, $Mg^{2+}$, $Ca^{2+}$, $Ba^{2+}$, $Cu^{2+}$, $La^{3+}$, $Ce^{3+}$, $Ce^{4+}$, $Eu^{3+}$, $Ti^{3+}$, $Ti^{4+}$, $Ag^+$, $Rh^{2+}$, $Rh^{3+}$, $Ru^{2+}$, $Ru^{3+}$, $M^2$ is at least one metal ion selected from the group consisting of $Fe^{2+}$, $Fe^{3+}$, $Co^{2+}$, $Co^{3+}$, $Mn^{2+}$, $Mn^{3+}$, $V^{4+}$, $V^{5+}$, $Cr^{2+}$, $Cr^{3+}$, $Rh^{3+}$, $Ru^{2+}$, $Ir^{3+}$, A and X are each, independently of one another, an anion selected from the group consisting of halide, hydroxide, sulfate, carbonate, cyanide, thiocyanate, isocyanate, cyanate, carboxylate, oxalate, nitrate, nitrosyl, hydrogensulfate, phosphate, dihydrogenphosphate, hydrogenphosphate and hydrogencarbonate, L is a water-miscible ligand selected from the group consisting of alcohols, aldehydes, ketones, ethers, polyethers, esters, polyesters, polycarbonate, ureas, amides, primary, secondary and tertiary amines, ligands having a pyridine nitrogen, nitriles, sulfides, phosphides, phosphites, phosphanes, phosphonates and phosphates, k is a fraction or integer greater than or equal to zero, and P is an organic additive, a, b, c, d, g and n are selected so that the compound (I) is electrically neutral, with c being able to be 0, e is the number of ligand molecules and is a fraction or integer greater than 0 or is 0, f and h are each, independently of one another, a fraction or integer greater than 0 or 0, wherein the reaction is carried out at a temperature of from 130° C. to 155° C.

According to the invention, the reaction of the at least one alkylene oxide selected from the group consisting of ethylene oxide, propylene oxide, butylene oxide, pentylene oxide and decene oxide with at least one starter compound is carried out at a temperature of from 130° C. to 155° C., preferably from 140° C. to 155° C., particularly preferably from 140° C. to 150° C.

The entire reaction is carried out in the temperature range specified. This leads to the induction phase being shortened compared to the conventional mode of operation at lower temperatures and the operating life of the catalyst being improved. At temperatures above the specified temperature range, it is possible for the catalyst activity to decrease during the reaction, especially in the case of ethoxylation. As a result, the reactions proceed with higher yields and products containing a reduced proportion of residue alcohol and also alkoxylated compounds having a low degree of alkoxylation are obtained. Furthermore, the residue alcohol content is, surprisingly, reduced even at the same degree of alkoxylation of the products when the reaction temperature is increased to at least 130° C., preferably at least 140° C.

The reaction can be carried out at constant temperature or else using a particular temperature profile, for example a temperature rising during the reaction, with the temperatures being within the above-defined temperature range.

The temperature during the induction period can in principle be chosen freely. However, it can also be in the range from 130° C. to 155° C. during the induction period. For the purposes of the present invention, an induction period means that the alkoxylation reaction does not begin immediately after the alkylene oxide is brought into contact with the starter compound and the double metal cyanide compound, but is instead delayed by a certain time. This induction period is reflected, for example, in the fact that a certain pressure is built up in the reactor after introduction of a small amount of alkylene oxide and remains constant for a certain time and drops quickly at the end of the induction period. After the decrease in pressure, the reaction has started and further introduction of the alkylene oxide can be carried out.

In a preferred embodiment of the process of the invention, inert gas is firstly introduced into the reactor and the alkylene oxide or oxides is/are subsequently added. This mode of operation has the advantage that, particularly when the alkylene oxide is ethylene oxide, the concentration of ethylene oxide in the gas phase can be kept so low that the gas-phase decomposition of the ethylene oxide can be reduced, in particular largely avoided.

In the process of the invention, the reaction vessel can, for example, firstly be charged with a suspension of alcohol and DMC catalyst. The catalyst can subsequently be activated by removal of water, e.g. by heating and/or evaporating the reaction vessel.

The reaction mixture is then advantageously heated to the reaction temperature and a prepressure of nitrogen is set. During the further course of the process, an initial amount of ethylene oxide, for example, is fed in. After the reaction has started, further ethylene oxide is fed in, and the reaction mixture is stirred until all the ethylene oxide has reacted. The reaction mixture can, if appropriate, be worked up further.

In a preferred embodiment, inert gas is added in addition to the alkylene oxide or oxides. Inert gases which are suitable for the purposes of the present invention are, for example, nitrogen, $CO_2$ or noble gases such as argon or mixtures thereof, preferably nitrogen.

The partial pressure of the inert gas during the reaction is from 0 to 20 bar, preferably from 0 to 10 bar, in particular from 0 to 6 bar, in the case of ethoxylation from 1.5 to 20 bar, preferably from 1.5 to 10 bar, in particular from 1.5 to 6 bar.

The pressure of the alkylene oxide or oxides during the reaction is from 0 to 10 bar, preferably from 0 to 6 bar, in particular from 0 to 3 bar.

According to the invention, the pressure changes during the reaction. When the reaction starts, the pressure initially drops somewhat. However, this is dependent on the speed at which the alkylene oxide is fed in. If an inert gas is present, this is compressed as the fill level in the reactor rises and at least its partial pressure is increased.

In one embodiment of the present invention, preference is given to the sum of inert gas partial pressure and alkylene oxide partial pressure, in particular the sum of inert gas partial pressure and ethylene oxide partial pressure, during the induction phase is from 0 to 20 bar, for example from 0 to 10 bar, in particular from 1.5 to 6.0 bar, preferably from 1.5 to 5.0 bar, particularly preferably from 1.5 to 3.0 bar.

In a further embodiment, the present invention therefore provides a process in which the reaction is carried out in the above-defined temperature range and the sum of inert gas partial pressure and alkylene oxide partial pressure, in particular the sum of inert gas partial pressure and ethylene oxide partial pressure, in from 1.5 bar to 6.0 bar during the induction phase.

The process of the invention is carried out using at least one alkylene oxide selected from the group consisting of ethylene oxide, propylene oxide, butylene oxide, pentylene oxide and decene oxide, preferably selected from the group consisting of ethylene oxide, propylene oxide and butylene oxide.

In a preferred embodiment, the present invention provides a process in which the alkylene oxide is ethylene oxide. However, it is likewise possible according to the invention for the alkylene oxide to be propylene oxide.

For safety reasons, a concentration of >40%, preferably >50%, of ethylene oxide in the gas phase in the reactor should be avoided, since spontaneous EO decomposition and thus superheating or explosion of the reactor can occur at high concentrations. Ethylene oxide in particular is therefore mixed with an inert gas for the purposes of the present invention.

Apart from the at least one alkylene oxide, a further alkylene oxide can also be added in the process of the present invention. A further alkylene oxide selected from the group consisting of ethylene oxide, propylene oxide, butylene oxide, pentylene oxide and decene oxide can advantageously be added. For the purposes of the present invention, preference is given to using propylene oxide or ethylene oxide together with less than 50% by mass of a further alkylene oxide, preferably less than 25%, in particular less than 5%, particularly preferably less than 1%. Preference is also given to the use of ethylene oxide or propylene oxide without addition of further alkylene oxides.

The process of the invention for preparing an alkoxylate is carried out in the presence of a double metal cyanide compound of the general formula I as catalyst:

$$M^1{}_a[M^2(CN)_b(A)_c]_d \cdot fM^1{}_g X_n \cdot h(H_2O) \cdot eL \cdot kP \qquad (I),$$

where $M^1$ is at least one metal ion selected from the group consisting of $Zn^{2+}$, $Fe^{2+}$, $Fe^{3+}$, $Co^{3+}$, $Ni^{2+}$, $Mn^{2+}$, $Co^{2+}$, $Sn^{2+}$, $Pb^{2+}$, $Mo^{4+}$, $Mo^{6+}$, $Al^{3+}$, $V^{4+}$, $V^{5+}$, $Sr^{2+}$, $W^{4+}$, $W^{6+}$, $Cr^{2+}$, $Cr^{3+}$, $Cd^{2+}$, $Hg^{2+}$, $Pd^{2+}$, $Pt^{2+}$, $V^{2+}$, $Mg^{2+}$, $Ca^{2+}$, $Ba^{2+}$, $Cu^{2+}$, $La^{3+}$, $Ce^{3+}$, $Ce^{4+}$, $Eu^{3+}$, $Ti^{3+}$, $Ti^{4+}$, $Ag^+$, $Rh^{3+}$, $Rh^{3+}$, $Ru^{2+}$, $Ru^{3+}$, $M^2$ is at least one metal ion selected from the group consisting of $Fe^{2+}$, $Fe^{3+}$, $Co^{2+}$, $Co^{3+}$, $Mn^{2+}$, $Mn^{3+}$, $V^{4+}$, $V^{5+}$, $Cr^{2+}$, $Cr^{3+}$, $Rh^{3+}$, $Ru^{2+}$, $Ir^{3+}$, A and X are each, independently of one another, an anion selected from the group consisting of halide, hydroxide, sulfate, carbonate, cyanide, thiocyanate, isocyanate, cyanate, carboxylate, oxalate, nitrate, nitrosyl, hydrogensulfate, phosphate, dihydrogenphosphate, hydrogenphosphate and hydrogencarbonate, L is a water-miscible ligand selected from the group consisting of alcohols, aldehydes, ketones, ethers, polyethers, esters, polyesters, polycarbonate, ureas, amides, primary, secondary and tertiary amines, ligands having a pyridine nitrogen, nitriles, sulfides, phosphides, phosphites, phosphanes, phosphonates and phosphates, k is a fraction or integer greater than or equal to zero, and P is an organic additive, a, b, c, d, g and n are selected so that the compound (I) is electrically neutral, with c being able to be 0, e is the number of ligand molecules and is a fraction or integer greater than 0 or is 0, f and h are each, independently of one another, a fraction or integer greater than 0 or 0.

Organic additives P which may be mentioned are: polyethers, polyesters, polycarbonates, polyalkylene glycol sorbitan esters, polyalkylene glycol glycidyl ethers, polyacrylamide, poly(acrylamide-co-acrylic acid), polyacrylic acid, poly(acrylamide-co-maleic acid), polyacrylonitrile, polyalkyl acrylates, polyalkyl methacrylates, polyvinyl methyl ether, polyvinyl ethyl ether, polyvinyl acetate, polyvinyl alcohol, poly-N-vinylpyrrolidone, poly(N-vinylpyrrolidone-co-acrylic acid), polyvinyl methyl ketone, poly(4-vinylphenol), poly(acrylic acid-co-styrene), oxazoline polymers, polyalkylenimines, maleic acid and maleic anhydride copolymers, hydroxyethylcellulose, polyacetates, ionic surface- and interface-active compounds, bile acids or their salts, esters or amides, carboxylic esters of polyhydric alcohols and glycosides.

These catalysts can be crystalline or amorphous. When k is equal to zero, crystalline double metal cyanide compounds are preferred. When k is greater than zero, crystalline, partially crystalline and also substantially amorphous catalysts are preferred.

There are various preferred embodiments of the modified catalysts. Catalysts of the formula (I) in which k is greater than zero constitute one preferred embodiment. The preferred catalyst then comprises at least one double metal cyanide compound, at least one organic ligand and at least one organic additive P.

In another preferred embodiment, k is equal to zero, e is optionally also equal to zero and X is exclusively a carboxylate, preferably formate, acetate or propionate. Such catalysts are described in WO 99/16775. In this embodiment, crystalline double metal cyanide catalysts are preferred. Also preferred are double metal cyanide catalysts as described in WO 00/74845 which are crystalline and platelet-like.

In a preferred embodiment, the present invention therefore provides a process in which the double metal cyanide compound used as catalyst is crystalline.

The modified catalysts are prepared by combining a metal salt solution with a cyanometalate solution which can optionally further comprise both an organic ligand L and an organic additive P. The organic ligand and optionally the organic additive are subsequently added. In a preferred embodiment of the catalyst preparation, an inactive double metal cyanide phase is prepared first and this is subsequently converted by recrystallization into an active double metal cyanide phase, as described in PCT/EP01/01893.

In another preferred embodiment of the catalysts, f, e and k are different from zero. The catalysts are then double metal cyanide catalysts containing a water-miscible organic ligand (generally in an amount of from 0.5 to 30% by weight), and an organic additive (generally in an amount of from 5 to 80% by weight), as described in WO 98/06312. The catalysts can be prepared either with intensive stirring (24 000 rpm using a Turrax) or with stirring, as described in U.S. Pat. No. 5,158,922.

Catalysts suitable for the alkoxylation are in particular double metal cyanide compounds containing zinc, cobalt or iron or two of these. A particularly useful catalyst is, for example, Berlin blue.

Preference is given to using crystalline DMC compounds. In a preferred embodiment, a crystalline DMC compound of the Zn—Co type containing zinc acetate as further metal salt component is used as catalyst. Such compounds crystallize in the monoclinic system and have a platelet-like habit. Such compounds are described, for example, in WO 00/74845 or PCT/EP01/01893.

DMC compounds suitable as catalysts can in principle be prepared in all ways known to those skilled in the art. For example, the DMC compounds can be prepared by direct precipitation, by the "incipient wetness" method, by preparation of a precursor phase and subsequent recrystallization.

The DMC compounds can be used as powder, paste or suspension or can be shaped to produce a shaped body, be incorporated into shaped bodies, foams or the like or be applied to shaped bodies, foams or the like.

The catalyst concentration used for the alkoxylation, based on the final quantities, is typically less than 2000 ppm (i.e. mg of catalyst per kg of product), preferably less than 1000 ppm, in particular less than 500 ppm, particularly preferably less than 100 ppm, for example less than 50 ppm or less than 35 ppm, very particularly preferably less than 25 ppm.

In a preferred embodiment, the present invention provides a process in which the double metal cyanide compound is used in an amount of 100 ppm or less, based on the final quantities.

In further embodiments, the present invention provides a process in which at least one of the following properties is fulfilled:

(1) $M^1$ is selected from the group consisting of $Zn^{2+}$, $Fe^{2+}$, $Fe^{3+}$, $Co^{3+}$, $Ni^{2+}$, $Mn^{2+}$, $Co^{2+}$, (2) $M^2$ is selected from the group consisting of $Fe^{2+}$, $Fe^{3+}$, $Co^{3+}$, or particularly preferably a process in which $M^1$ is $Zn^{2+}$ and $M^2$ is $Co^{3+}$.

Suitable starter compounds are all compounds which have an active hydrogen. According to the invention, preference is given to OH-functional compounds as starter compounds.

Particularly preferred starter compounds are monofunctional or polyfunctional alcohols having from 2 to 24 carbon atoms, preferably monofunctional linear or singly or multiply branched alkanols having from 2 to 24 carbon atoms.

Suitable branched alcohols have the hydroxyl group in, for example, the 2, 3, 4, etc. position. The alkyl group can be linear or branched again and bear, for example, methyl or ethyl substituents.

Examples of suitable alcohols are 2-decanol, 2-dodecanol, 2-tetradecanol, 2-hexadecanol, in each case obtainable by addition of water onto a-olefins, (6-ethyl)-2-nonanol, obtainable by reaction of 2-ethylhexanol with acetone and subsequent hydrogenation, (7-ethyl)-3-decanol and (3-methyl-6-ethyl)-2-nonanol, obtainable by reaction of 2-ethylhexanol with methyl ethyl ketone and subsequent hydrogenation, 2-hexadecanol and 2-octadecanol, obtainable by reaction of $C_{13}/C_{15}$-aldehyde with acetone, 3-nonadecanol and (3-methyl)-2-octadecanol, (3-methyl)-2-hexadecanol, 3-heptadecanol, obtainable by reaction of $C_{13}/C_{15}$-aldehyde with methyl ethyl ketone. The reaction products based on $C_{13}/C_{15}$-aldehyde are about 40-50% branched in the alpha position in the technical-grade mixtures.

Examples of further suitable alcohols are linear $C_{12}/C_{14}$-alkanes having a hydroxyl group in a nonterminal position along the chain or mixtures thereof (e.g. Softanol® alcohols from Nippen Shokubai or Tergitol® alcohols from Dow).

Particularly useful starter compounds for use in the process of the invention are monofunctional linear or singly or multiply branched alcohols having from 6 to 18 carbon atoms, preferably alcohols having from 8 to 15 carbon atoms, in particular from 10 to 15 carbon atoms, for example tridecanol or propylheptanol or mixtures of $C_{13}$- and $C_{15}$-alcohols.

Alcohols suitable for the purposes of the invention are thus in particular octanol, 2-ethylhexanol, nonanol, decanol, undecanol, dodecanol, 2-butyloctanol, tridecanol, tetradecanol, pentadecanol, isooctanol, isononanol, isodecanol, isoundecanol, isododecanol, isotridecanol isotetradecanol, isopentadecanol, preferably isodecanol, 2-propylheptanol, tridecanol, isotridecanol or mixtures of C13- to C15-alcohols.

The present invention therefore also provides, in a preferred embodiment, a process in which the starter compound is a monofunctional linear or branched alcohol having from 2 to 24, preferably from 8 to 15, carbon atoms.

For example, the alcohols used as starter compound for the purposes of the invention can be Guerbet alcohols, in particular ethylhexanol, propylheptanol, butyloctanol. The present invention therefore also provides, in a particularly preferred embodiment, a process in which the starter compound is a Guerbet alcohol.

According to the invention, the alcohols used as starter compound can also be mixtures of various isomers. For example, propylheptanol can be obtained from valeraldehyde by aldol condensation and subsequent hydrogenation. The preparation of valeraldehyde and the corresponding isomers is carried out by hydroformylation of butene, as described, for example, in U.S. Pat. No. 4,287,370; Beilstein E IV 1, 32 68, Ullmanns Encyclopedia of Industrial Chemistry, 5th edition, volume A1, pages 323 and 328 ff. The subsequent aldol condensation is described, for example, in U.S. Pat. No. 5,434,313 and Rompp, Chemie Lexikon, 9th edition, key word "Aldol-Addition", page 91. The hydrogenation of the aldol condensation product is carried out under customary hydrogenation conditions.

In a preferred embodiment, the present invention therefore provides a process in which the starter compound is 2-propylheptanol or an isomer mixture thereof. For the purposes of the present patent application, an isomer mixture of 2-propylheptanol is the mixture of 2-propylheptanol with primary aliphatic alcohols having the same empirical formula. These are preferably compounds obtained as by-products in the preparation of 2-propylheptanol.

Furthermore, 2-propylheptanol can be prepared by condensation of 1-pentanol (as a mixture of the corresponding methyl-1-butanols) in the presence of KOH at elevated temperatures, cf., for example, Marcel Guerbet, C. R. Acad Sci Paris 128, 511, 1002 (1899). Reference may also be made to Rompp, Chemie Lexikon, 9th edition, Georg Thieme Verlag Stuttgart, and the references cited therein and also Tetrahedron, vol. 23, pages 1723 to 1733.

Secondary alcohols or mixtures are also suitable. These can be obtained, for example, by addition of ketones onto aldehydes with subsequent hydrogenation as described in DE-A-100 35 617. Preference is given here to methyl ketones such as acetone, methyl ethyl ketone or methyl isobutyl ketone. Paraffin oxidation products formed, for example, by Bashkirov oxidation are also suitable. Here, products from $C_{11}$-$C_{16}$-paraffin mixtures, especially products from $C_{12-14}$-paraffin mixtures, are preferred. Further suitable alcohols are, for example, secondary alcohols which are obtained by addition of water onto olefins or by free-radical or other oxidation of olefins.

In the process of the invention, the alkylene oxide mixture is preferably used in such amounts that the degree of alkoxylation obtained is, for example, in the range from 2 to 20, preferably in the range from 2.5 to 14, particularly preferably in the range from 3 to 6.

In addition, the present invention also provides alkoxylates obtainable by a process as described above.

In a preferred embodiment of the present invention, the alkoxylate is an ethoxylate. These compounds display good wetting properties on hard surfaces and good emulsifying behavior.

The alkoxylates of the invention display good wetting on hard surfaces. The advantageous wetting behavior of the mixtures according to the invention can be determined, for example, by measuring the contact angle on glass, polyethylene oxide or steel.

The present invention therefore also provides for the use of an alkoxylate according to the invention or an alkoxylate obtainable by a process according to the invention as emulsifier, foam regulator and as wetting agent for hard surfaces, in particular the use in laundry detergents, surfactant formulations for cleaning hard surfaces, humectants, cosmetic, pharmaceutical and crop protection formulations, paints and varnishes, coating compositions, adhesives, leather degreasing compositions, formulations for the textile industry, fiber processing, metal processing, the food industry, water treatment, the paper industry, fermentation or mineral processing and in emulsion polymerizations.

Furthermore, the alkoxylates prepared according to the invention serve to reduce surface tension, for example in aqueous surfactant formulations. The reduced surface tension can be determined, for example, by the pendant drop method. This also results in improved effectiveness of the alkoxylates of the invention as emulsifier or coemulsifier. The alkoxylates of the invention can also be used for reducing the surface tension at short times of usually less than one second or for accelerating the establishment of the surface tension in aqueous surfactant formulations.

Preferred fields of application of the alkoxylates of the invention are described in more detail below.

The alkoxylates prepared according to the invention are preferably used in the following fields:

Surfactant formulations for cleaning hard surfaces: suitable surfactant formulations to which the alkoxylates of the invention can be added are described, for example, in Formulating Detergents and Personal Care Products by Louis Ho Tan Tai, AOCS Press, 2000.

As further components, they comprise, for example, soap, anionic surfactants such as LAS or paraffin sulfonates or FAS or FAES, acids such as phosphoric acid, amidosulfonic acid, citric acid, lactic acid, acetic acid, other organic and inorganic acids, solvents such as ethylene glycol, isopropanol, complexing agents such as EDTA, NTA, MGDA, phosphonates, polymers such as polyacrylates, copolymers of maleic acid-acrylic acid, alkaline sources such as hydroxides, silicates, carbonates, perfume oils, oxidants such as perborates, peracids or trichloroisocyanuric acid, Na or K dichloroisocyanurates, enzymes; see also Milton J. Rosen, Manilal Dahanayake, Industrial Utilization of Surfactants, AOCS Press, 2000 and Nikolaus Schonfeldt, Grenzflachenaktive Ethylenoxidaddukte. Here, formulations for the other applications mentioned are also dealt with in principle. They can be household cleaners such as all-purposes cleaners, dishwashing detergents for manual and automatic washing of dishes, metal degreasing, industrial applications such as cleaners for the food industry, bottle washing, etc. They can also be cleaners for pressure rollers and pressure plates in the printing industry. Suitable further constituents are known to those skilled in the art.

Humectants, in particular for the printing industry.

Cosmetic, pharmaceutical and crop protection formulations. Suitable crop protection formulations are described, for example, in EP-A-0 050228. Customary further constituents can be present in crop protection compositions.

Paints and varnishes, coating compositions, colored coatings, pigment preparations and adhesives in the surface coatings and films industries.

Leather degreasing compositions.

Formulations for the textile industry, e.g. leveling agents, or formulations for yarn cleaning.

Fiber processing and auxiliaries for the pulp and paper industry.

Metal processing, e.g. metal finishing and electroplating.

Food industry.

Water treatment and drinking water production.

Fermentation.

Mineral processing and dust control.

Building auxiliaries.

Emulsion polymerization and preparation of dispersions.

Coolants and lubricants.

Such formulations usually comprise constituents such as surfactants, builders, fragrances and dyes, complexing agents, polymers and other constituents. Typical formulations are described, for example, in WO 01/32820. Further constituents suitable for various applications are described by way of example in EP-A-0 620 70, WO 95/27034, EP-A-0 681 865, EP-A-0 616 026, EP-A-0 616 028, DE-A-42 37 178 and U.S. Pat. No. 5,340,495 and in Schönfeldt, see above.

In general, the alkoxylates prepared according to the invention can be used in all fields in which the action of surface-active substances is necessary.

The present invention therefore also provides laundry detergents, cleaners, wetting agents, coating compositions, adhesives, leather degreasing compositions, humectants or textile treatment compositions or cosmetic, pharmaceutical or crop protection formulations comprising an alkoxylate according to the invention or an alkoxylate obtainable by a process according to the invention. The compositions preferably contain from 0.1 to 20% by weight of the alkoxylates.

The present invention is illustrated below by means of examples.

EXAMPLES

Preparative Example

Catalyst 16 000 g of aqueous hexacyanocobaltic acid (cobalt content: 9 g/l) were placed in a stirred vessel having a volume of 30 l and equipped with a propeller stirrer, immersed tube for metered addition, pH sensor and scattered light sensor and were heated to 50° C. whilst stirring. 9224 g of aqueous zinc acetate dihydrate solution (zinc content: 2.6% by weight), which had likewise been heated to 50° C., was subsequently fed in over a period of 15 minutes whilst stirring at a stirrer power of 0.4 W/l.

351 g of Pluronic® PE 6200 (BASF AG) were added to this precipitation suspension and the mixture was stirred for a further 10 minutes.

A further 3690 g of aqueous zinc acetate dihydrate solution (zinc content: 2.6% by weight) were subsequently metered in over a period of 5 minutes whilst stirring at a stirrer power of 1 W/l. The suspension was stirred for another 2 hours. The pH dropped from 4.02 to 3.27 during this time and then remained constant. The precipitation suspension obtained in this way was subsequently filtered and the solid was washed on the filter with 6 times the cake volume of water.

The moist filter cake was dried and dispersed in Tridekanol® N by means of a slotted rotor mill. The suspension obtained in this way had a multimetal cyanide content of 5% by weight.

Comparative Example 1

Induction Behavior 316 g (2.0 mol) of 2-propyl-1-heptanol (isomer mixture of 87% of 2-propyl-1-heptanol, 11% of 2-propyl-4-methy-1-hexanol, <1% of 2-propyl-5-methyl-1-hexanol) and 35 ppm of double metal cyanide catalyst were dewatered for two hours at a temperature of 100° C. and about 20 mbar in a 2 l pressure autoclave. The autoclave was subsequently flushed three times with nitrogen and then heated to the desired temperature. After the temperature had been reached, a total of 30 g of ethylene oxide were metered in whilst stirring. The time (induction time) from the commencement of the metered addition to the commencement of the reaction was determined. The commencement of the reaction can be recognized by the associated evolution of heat and thus an increase in the temperature of the reaction mixture.

| Temperature | Induction time |
| --- | --- |
| 100° C. | did not start |
| 120° C. | 20 min |
| 140° C. | 5 min |
| 160° C. | 5 min |

Comparative Example 2 (2-propylheptanol+8 EO at 160° C.)

316 g (2.0 mol) of 2-propyl-1-heptanol (isomer mixture of 87% of 2-propyl-1-heptanol, 11% of 2-propyl-4-methy-1-hexanol, <1% of 2-propyl-5-methyl-1-hexanol) and 35 ppm of double metal cyanide catalyst (based on the product) were dewatered for two hours at a temperature of 100° C. and about 20 mbar in a pressure autoclave. The autoclave was subsequently flushed three times with nitrogen and then heated to 160° C. After this temperature had been reached, a total of 704 g (16.0 mol) of ethylene oxide were to be metered in whilst stirring. After addition of 572 g of ethylene oxide, a satisfactory reaction could no longer be detected (hardly any decrease in pressure, hardly any evolution of heat).

Comparative Example 3 (2-propylheptanol+1.2 PO+6 EO at 160° C.)

316 g (2.0 mol) of 2-propyl-1-heptanol and 35 ppm of double metal cyanide catalyst (based on the product) were dewatered for two hours at a temperature of 100° C. and about 20 mbar in a pressure autoclave. The autoclave was subsequently flushed three times with nitrogen and then heated to 160° C. After this temperature had been reached, a total of 140 g (2.4 mol) of propylene oxide were metered in at 160° C. whilst stirring. After the metered addition of the PO was complete, the mixture was stirred at 160° C. for another 15 minutes. 528 g (12.0 mol) of ethylene oxide were then to be metered in. After addition of 444 g of ethylene oxide, a satisfactory reaction could no longer be detected (hardly any decrease in pressure, hardly any evolution of heat).

Example 1 (2-Dropylheptanol+8 EO at 140° C.)

316 g (2.0 mol) of 2-propyl-1-heptanol (isomer mixture of 87% of 2-propyl-1-heptanol, 11% of 2-propyl-4-methy-1-hexanol, <1% of 2-propyl-5-methyl-1-hexanol) and 35 ppm of double metal cyanide catalyst (based on the product) were dewatered for two hours at a temperature of 100° C. and about 20 mbar in a pressure autoclave. The autoclave was subsequently flushed three times with nitrogen and then heated to 140° C. After this temperature had been reached, a total of 704 g (16.0 mol) of ethylene oxide were metered in whilst stirring. After the metered addition of ethylene oxide was complete, the mixture was stirred for another 1 hour at 140° C., the autoclave was then cooled to 80° C., flushed three times with nitrogen, then evacuated to 20 mbar to degas the reaction mixture and the reactor was emptied. The reaction product was not filtered and corresponded to the desired product.

Example 2 (pure 2-propylheptanol+1.2 PO+6 EO at 140° C.)

316 g (2.0 mol) of 2-propyl-1-heptanol and 35 ppm of double metal cyanide catalyst (based on the product) were dewatered for two hours at a temperature of 100° C. and about 20 mbar in a pressure autoclave. The autoclave was subsequently flushed three times with nitrogen and then heated to 140° C. After this temperature had been reached, a total of 140 g (2.4 mol) of propylene oxide at 140° C. were metered in whilst stirring. After the metered addition of PO was complete, the mixture was stirred at 140° C. for another 15 minutes and the metered addition of a total of 528 g (12.0 mol) of ethylene oxide was then commenced. After the metered addition of ethylene oxide was complete, the mixture was stirred for another 1 hour at 140° C., the autoclave was then cooled to 80° C., flushed three times with nitrogen, then evacuated to 20 mbar to degas the reaction mixture and the reactor was emptied. The reaction product was not filtered and corresponded to the desired product.

Example 3 (2-propylheptanol+1.2 PO+6 EO at 140° C. and a maximum of 2.0 bar EO pressure)

316 g (2.0 mol) of 2-propyl-1-heptanol (isomer mixture of 87% of 2-propyl-1-heptanol, 11% of 2-propyl-4-methyl-1-hexanol, <1% of 2-propyl-5-methyl-1-hexanol) and 35 ppm of double metal cyanide catalyst (based on the product) were dewatered for two hours at a temperature of 100° C. and about 20 mbar in a pressure autoclave. The autoclave was subsequently flushed three times with nitrogen and then heated to 140° C. After this temperature had been reached, a total of 140 g (2.4 mol) of propylene oxide at 140° C. were metered in whilst stirring. After the metered addition of PO was complete, the mixture was stirred at 140° C. for another 15 minutes.

A total pressure of 2.0 bar of nitrogen (absolute) was then set at 140° C. and the metered addition of a total of 528 g (12.0 mol) of ethylene oxide at a total pressure of not more than 4.0 bar (absolute, 140° C.) was then commenced. After the metered addition of ethylene oxide was complete, the mixture was stirred for another 1 hour at 140° C., the autoclave was then cooled to 80° C., flushed three times with nitrogen, then evacuated to 20 mbar to degas the reaction mixture and the reactor was emptied. The reaction product was not filtered and corresponded to the desired product.

Example 4 (2-propylheptanol+8 EO at 150° C. and 2.25 bar EO pressure)

316 g (2.0 mol) of 2-propyl-1-heptanol and 35 ppm of double metal cyanide catalyst (based on the product) were dewatered for two hours at a temperature of 100° C. and about 20 mbar in a pressure autoclave. The autoclave was subsequently flushed three times with nitrogen and a total pressure of 2.25 bar of nitrogen (absolute) was then set at 150° C. After this temperature had been reached, a total of 704 g (16.0 mol) of ethylene oxide were metered in at a total pressure of not more than 4.5 bar (absolute at 150° C.) whilst stirring. After the metered addition of ethylene oxide was complete, the mixture was stirred for another 1 hour at 150° C., the autoclave was then cooled to 80° C., flushed three times with nitrogen, then evacuated to 20 mbar to degas the reaction mixture and the reactor was emptied. The reaction product was not filtered and corresponded to the desired product.

Example 5 (2-propylheptanol+0.8 PO)

316 g (2.0 mol) of 2-propyl-1-heptanol (isomer mixture of 87% of 2-propyl-1-heptanol, 11% of 2-propyl-4-methyl-1-hexanol, <1% of 2-propyl-5-methyl-1-hexanol) and 35 ppm of double metal cyanide catalyst (based on the product) were dewatered for two hours at a temperature of 100° C. and about 20 mbar in a pressure autoclave. The autoclave was subsequently flushed three times with nitrogen and then heated to 140° C. After this temperature had been reached, a total of 93 g (1.6 mol) of propylene oxide at 140° C. were metered in whilst stirring. After the metered addition of PO was complete, the mixture was stirred at 140° C. for another 15 minutes, the autoclave was flushed three times with nitrogen, then evacuated to 20 mbar to degas the reaction mixture, the autoclave was then cooled to 80° C. and the reactor was emptied.

Residue alcohol content (2-propyl-1-heptanol): 28.6%

Example 6 (2-propylheptanol+1.0 PO)

The procedure of example 5 was repeated, but 2.0 mol of propylene oxide instead of 1.6 mol were added and a reaction temperature of 140° C. was employed.

Residue alcohol content (2-propyl-1-heptanol): 24.2%

Example 7 (2-propylheptanol+1.20 PO)

The procedure of example 5 was repeated, but 2.4 mol of propylene oxide instead of 1.6 mol were added and a reaction temperature of 160° C. was employed.

Residue alcohol content (2-propyl-1-heptanol): 20.0%

Example 8 (2-propylheptanol+1.20 PO)

The procedure of example 5 was repeated, but 2.4 mol of propylene oxide instead of 1.6 mol were added and a reaction temperature of 140° C. was employed.

Residue alcohol content (2-propyl-1-heptanol): 19.8%

Example 9 (2-propylheptanol +1.23 PO)

The procedure of example 5 was repeated, but 2.46 mol of propylene oxide instead of 1.6 mol were added and a reaction temperature of 120° C. was employed.

Residue alcohol content (2-propyl-1-heptanol): 20.8%

Example 10 (2-propylheptanol+1.28 PO)

The procedure of example 5 was repeated, but 2.56 mol of propylene oxide instead of 1.6 mol were added and a reaction temperature of 140° C. was employed.

Residue alcohol content (2-propyl-1-heptanol): 17.7%

Example 11 (2-propylheptanol+1.30 PO)

The procedure of example 5 was repeated, but 2.6 mol of propylene oxide instead of 1.6 mol were added and a reaction temperature of 140° C. was employed.

Residue alcohol content (2-propyl-1-heptanol): 17.6%

Example 12 (2-propylheptanol+1.40 PO)

The procedure of example 5 was repeated, but 2.8 mol of propylene oxide instead of 1.6 mol were added and a reaction temperature of 140° C. was employed.

Residue alcohol content (2-propyl-1-heptanol): 15.8%

Example 13 (2-propylheptanol+1.44 PO)

The procedure of example 5 was repeated, but 2.88 mol of propylene oxide instead of 1.6 mol were added and a reaction temperature of 140° C. was employed.

Residue alcohol content (2-propyl-1-heptanol): 14.8%

Example 14 (2-propylheptanol+1.51 PO)

The procedure of example 5 was repeated, but 3.02 mol of propylene oxide instead of 1.6 mol were added and a reaction temperature of 120° C. was employed.

Residue alcohol content (2-propyl-1-heptanol): 15.0%

Example 15 (2-propylheptanol+1.63 PO)

The procedure of example 5 was repeated, but 3.26 mol of propylene oxide instead of 1.6 mol were added and a reaction temperature of 160° C. was employed.

Residue alcohol content (2-propyl-1-heptanol): 10.1%

Example 16 (2-propylheptanol+1.71 PO)

The procedure of example 5 was repeated, but 3.42 mol of propylene oxide instead of 1.6 mol were added and a reaction temperature of 120° C. was employed.

Residue alcohol content (2-propyl-1-heptanol): 10.7%

The invention claimed is:

1. A process for preparing at least one alkoxylate, which comprises:

bringing at least one alkylene oxide selected from the group consisting of ethylene oxide, propylene oxide, butylene oxide, pentylene oxide, and decene oxide into contact with at least one Guerbet alcohol having from 10 to 15 carbon atoms in the presence of at least one double metal cyanide compound of the general formula (I):

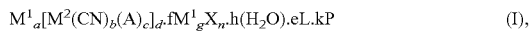

$$M^1_a[M^2(CN)_b(A)_c]_d \cdot fM^1_gX_n \cdot h(H_2O) \cdot eL \cdot kP \quad (I),$$

wherein $M^1$ is at least one metal ion selected from the group consisting of $Zn^{2+}$, $Fe^{2+}$, $Fe^{3+}$, $Co^{3+}$, $Ni^{2+}$, $Mn^{2+}$, $Co^{2+}$, $Sn^{2+}$, $Pb^{2+}$, $Mo^{4+}$, $Mo^{6+}$, $Al^{3+}$, $V^{4+}$, $V^{5+}$, $Sr^{2+}$, $W^{4+}$, $W^{6+}$, $Cr^{2+}$, $Cr^{3+}$, $Cd^{2+}$, $Hg^{2+}$, $Pd^{2+}$, $Pt^{2+}$, $V^{2+}$, $Mg^{2+}$, $Ca^{2+}$, $Ba^{2+}$, $Cu^{2+}$, $La^{3+}$, $Ce^{3+}$, $Ce^{4+}$, $Eu^{3+}$, $Ti^{3+}$, $Ti^{4+}$, $Ag^+$, $Rh^{2+}$, $Rh^{3+}$, $Ru^{2+}$, and $Ru^{3+}$;

$M^2$ is at least one metal ion selected from the group consisting of $Fe^{2+}$, $Fe^{3+}$, $Co^{2+}$, $Co^{3+}$, $Mn^{2+}$, $Mn^{3+}$, $V^{4+}$, $V^{5+}$, $Cr^{2+}$, $Cr^{3+}$, $Rh^{3+}$, $Ru^{2+}$, and $Ir^{3+}$;

A and X are each, independently of one another, an anion selected from the group consisting of halide, hydroxide, sulfate, carbonate, cyanide, thiocyanate, isocyanate, cyanate, carboxylate, oxalate, nitrate, nitrosyl, hydrogensulfate, phosphate, dihydrogenphosphate, hydrogenphosphate, and hydrogencarbonate;

L is a water-miscible ligand selected from the group consisting of alcohols, aldehydes, ketones, ethers, polyethers, esters, polyesters, polycarbonate, ureas, amides, primary, secondary and tertiary amines, ligands having a pyridine nitrogen, nitriles, sulfides, phosphides, phosphites, phosphanes, phosphonates, and phosphates;

k is a fraction or integer greater than 0;

P is an organic additive selected from the group consisting of polyethers, polyesters, polycarbonates, polyalkylene glycol sorbitan esters, polyalkylene glycol glycidyl ethers, polyacrylamide, poly(acrylamide-co-acrylic acid), polyacrylic acid, poly(acrylamide-co-maleic acid), polyacrylonitrile, polyalkyl acrylates, polyalkyl methacrylates, polyvinyl methyl ether, polyvinyl ethyl ether, polyvinyl acetate, polyvinyl alcohol, poly-N-vinylpyrrolidone, poly(N-vinylpyrrolidone-co-acrylic acid), polyvinyl methyl ketone, poly(4-vinylphenol), poly(acrylic acid-co-styrene), oxazoline polymers, polyalkylenimines, maleic acid and maleic anhydride copolymers, hydroxyethylcellulose, polyacetates, ionic surface- and interface-active compounds, bile acids or their salts, esters or amides, carboxylic esters of polyhydric alcohols, glycosides and mixtures thereof;

a, b, c, d, g and n are selected so that the compound (I) is electrically neutral, wherein c may be equal to 0;

e is the number of ligand molecules and is a fraction or integer greater than or equal to 0;

f and h are each, independently of one another, a fraction or integer greater than or equal to 0; and wherein the reaction is carried out at a temperature of from 140 C. to 155° C.

2. The process according to claim 1, wherein (1) $M^1$ is selected from the group consisting of $Zn^{2+}$, $Fe^{2+}$, $Fe^{3+}$, $Co^{3+}$, $Ni^{2+}$, $Mn^{2+}$, and $Co^{2+}$; or (2) $M^2$ is selected from the group consisting of $Fe^{2+}$, $Fe^{3+}$, and $Co^{3+}$.

3. The process according to claim 1, wherein $M^1$ is $Zn^{2+}$ and $M^2$ is $Co^{3+}$.

4. The process according to claim 1, wherein the at least one alkylene oxide is ethylene oxide or propylene oxide.

5. The process according to claim 1, wherein the alcohol is 2-propylheptanol or an isomer mixture thereof.

6. The process according to claim 1, wherein the sum of inert gas partial pressure and alkylene oxide partial pressure is from 1.5 bar to 6.0 bar during the induction phase.

7. The process according to claim 1, wherein the Guerbet alcohol is selected from the group consisting of propylheptanol and butyl octanol.

8. The process according to claim 1, wherein the reaction is carried out at a temperature of from 140° C. to 150° C.

* * * * *